United States Patent [19]
Sheerin

[11] 3,978,139
[45] Aug. 31, 1976

[54] PROCESS OF PREPARING NAPHTHYL ACETALS

[75] Inventor: Thomas J. Sheerin, Edison, N.J.

[73] Assignee: Mobil Oil Corporation, New York, N.Y.

[22] Filed: Mar. 31, 1975

[21] Appl. No.: 563,874

[52] U.S. Cl............................................ 260/613 D
[51] Int. Cl.². ........................................ C07C 41/06
[58] Field of Search......... 260/613 R, 615 A, 613 D

[56] References Cited
UNITED STATES PATENTS

| | | | |
|---|---|---|---|
| 2,000,252 | 5/1935 | Reppe et al..................... | 260/615 A |
| 3,024,284 | 3/1962 | Howard et al. ............. | 260/615 A X |
| 3,497,181 | 2/1970 | Braid........................... | 260/613 R X |

*Primary Examiner*—Bernard Helfin
*Attorney, Agent, or Firm*—Charles A. Huggett; Raymond W. Barclay; Claude E. Setliff

[57] ABSTRACT

Naphthyl acetals are made by reacting a naphthol with an alkyl vinyl ether under the influence of an aliphatic acid catalyst. For example n-butyl-1-naphthyl acetal is made by reacting 1-naphthol with n-butyl vinyl ether in the presence of up to about 5 mole percent, based on moles of naphthol, of a weak organic acid such as acetic acid or other aliphatic monocarboxylic acids.

7 Claims, No Drawings

PROCESS OF PREPARING NAPHTHYL ACETALS

BACKGROUND OF THE INVENTION

1. Field of the Invention

This invention is concerned with a process of making naphthyl acetals. More particularly it is concerned with a method for making such acetals which involves the step of reacting a naphthol with an alkyl vinyl ether in the presence of an aliphatic acid catalyst.

2. Discussion of the Prior Art

The general process of making naphthyl acetals from naphthols and vinyl ethers is well known in the art. As described in U.S. Pat. No. 3,497,181, such method involves the reaction of naphthol and a vinyl ether. Specifically, it is disclosed therein that 1-naphthol may be reacted with n-butyl vinyl ether to yield n-butyl naphthyl acetal [designated as 1-n-butoxy-1(1-naphthoxy) ethane in Example 2 of the patent]. The patent discloses also that an acid catalyst such as p-toluene sulfonic acid can be used as catalyst in the reaction involving a vinyl ether and a hydroxyaromatic compound. But as will appear hereinafter, this acid, when used in the usual catalytic amount, is not a catalyst for the reaction of this invention.

SUMMARY OF THE INVENTION

The invention provides a process for making a compound of the formula

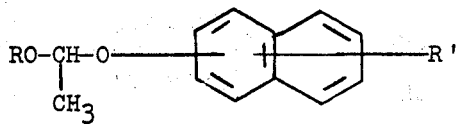

wherein R is a $C_2$-$C_{10}$ alkyl and R' is hydrogen or a $C_1$-$C_{20}$ alkyl, comprising the step of reacting a naphthol with a vinyl ether of the formula

RO-CH=CH$_2$ wherein R is an alkyl group of from 2 to 10 carbon atoms, in the presence of an aliphatic monocarboxylic acid having 1 to 20 carbon atoms.

DESCRIPTION OF SPECIFIC EMBODIMENTS

It is known that naphthol in small amounts is a superior antioxidant for lubricants. However, if the concentration exceeds a certain level it acts as an oxidation catalyst. It has been found that acetals such as n-butyl naphthyl acetal (hereinafter sometimes referred to as BNA) can be used as the source of naphthol because it decomposes thermally to the naphthol and butyl vinyl ether (hereinafter sometimes referred to as BVE). Ideally, it acts as a reservoir which continuously replaces the naphthol consumed as the lubricant ages, thereby eliminating the critical concentration encountered with naphthol per se.

Because of the tendency of BNA to decompose thermally, the temperatures at which the reaction to synthesize it can be run, whether catalyzed or uncatalyzed, is limited. In this connection, it has been found that the reaction can be safely run at from about 75°C to about 130°C, preferably at from about 95°C to about 105°C.

The reaction may be run in a solvent, but the usual solvents such as benzene, toluene and xylene cannot be expected to show any significant effect on the yield of product. Solvents such as ethanol, butanol and dimethylformamide should be avoided because of the reduced yields of product and of unusually high amounts of by-products.

The general reaction is shown as follows, using 1-naphthol and n-butyl vinyl ether as an example:

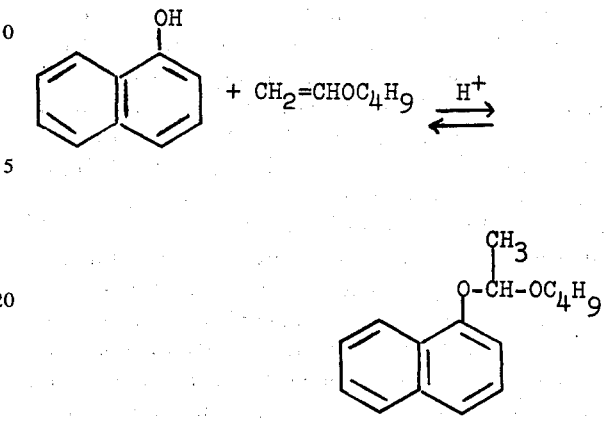

The naphthol and a solvent, such as toluene, are placed cold into a reactor, and an acid, such as acetic acid, is added and heating is accomplished under a nitrogen atmosphere. The vinyl ether is added as heating is continued. Depending upon the reactor's efficiency to remove heat, the latter reactant can be added over a period of from about 0.5 to about 10 hours, or more preferably about 1 hour to about 5 hours, the time selected also being dependent on the batch size. The time of addition of the vinyl ether is, however, not critical.

It has been surprisingly discovered that, while strong acids used in the usual catalytic amounts (of the order of 0.1 mole per mole of reactant), cannot be used because, it is believed, they cause homopolymerization of the vinyl ether as well as other side reactions, weak organic acids are suitable to catalyze the reactions involved in the herein disclosed process. Such acids, as has been stated, are those having from 1 to 20 carbon atoms, including acetic, propionic, hexanoic, nonanoic, dodecanoic, octadecanoic and eicosanoic (arachidic) acids. These are useful in a concentration range between about 0.1 mole percent to about 5 mole percent based on moles of naphthol, preferably 1 to 2%.

Although butyl naphthyl acetal, for example, is heat sensitive, the formation of this product, as well as the formation of others in the series, can be maintained and analyzed by gas chromatography if certain precautions are observed. In this regard, the injection point temperature seems to be important since a large majority of the degradation ostensibly occurs when the injection point temperature is too high. With respect to butyl naphthyl acetal per se, the temperature of the injection point should not exceed about 150°C. At higher temperatures, thermal breakdown of butyl naphthyl acetal to starting materials occurs, while at temperatures much below 150°C the product peaks become badly skewed because of improper volatilization. It should be understood that in the other products (i.e. when R is not butyl) this temperature will be higher or lower depending upon whether R is larger or smaller than butyl.

Having described the invention in a general way, the following is offered as specific illustrations.

EXAMPLE

The tables below summarize the results obtained in making n-butyl naphthyl acetal. In all cases, 1-naphthol was added to toluene at room temperature. The catalyst (if used) was added at this point and the mixture was heated to 100°C. The n-butyl vinyl ether was then added to the stirred mixture (through which $N_2$ was being bubbled) over a period of 1 hour. The amount of toluene was equal to about 14% of the total charge.

In three runs uncatalyzed by acids, the yields of n-butyl naphthyl acetal were 62, 71 and 79 percent respectively. These were atypical, however, since in 27 other runs (not acid catalyzed) using various grades of naphthol, varying amounts of excess of reactants, various solvent systems, pre-wash techniques and, in some runs, bases as catalysts, the yield of n-butyl naphthyl acetal never exceeded 48 percent, and the yields fell as low as 14 percent. Therefore, the normal expectation from a run not using an acid catalyst as defined herein is about 35 percent yield of n-butyl naphthyl acetal.

Table I contains results obtained using various acids. The table illustrates the invention and also shows results using other acids.

TABLE I

| Mole Percent | Catalyst | Yield of BNA | Residual Amount of BVE*, percent | Reaction Time, Hrs. |
| --- | --- | --- | --- | --- |
| 0.1 | p-toluene sulfonic acid | 0 | 8 | ½ |
| 5 | Filtrol clay (sulfonic) acid functional) | 0 | 0.9 | 1 |
| 0.1 | $FeCl_3.6H_2O$ | 1 | 9.6 | ½ |
| 1.0 | $FeCl_3.6H_2O$ | 0 | 2.3 | 1 |
| 2.0 | $BF_3(Phenol)_2$ | 0 | Polymerized | ½ |
| 2.0 | $BF_3(H_2O)_2$ | 0 | Polymerized | ½ |
| 0.1 | Acetic Acid | 51 | | 1 |
| 0.1 | Nonanoic Acid | 45 | | 22 |
| 1.0 | Acetic Acid | 72 | | 24 |
| 1.0 | Nonanoic Acid | 69 | | 24 |
| 2.0 | Acetic Acid | 75 | | 17 |

*BVE = n-butyl vinyl ether

TABLE II

Results Using Various Prewash Techniques

| Prewash Naphthol With | Yield of BNA | Reaction Time, Hours |
| --- | --- | --- |
| Water | 33 | 4 |
| 3 percent NaOH | 31 | 2 |
| 7.5 percent $H_2SO_4$ | 39 | 21 |
| 3 percent HCl | 40 | 22 |

TABLE III

Results With Various Base Catalysts

| Mole Percent | Catalyst | Yield of BNA | Reaction Time, Hours |
| --- | --- | --- | --- |
| 0.1 | 0.5 KOH in $CH_3OH$ | 36 | 21 |
| 0.1 | 0.5 N LiOH in $H_2O$ | 27 | 20 |
| 1.0 | 10 percent NaOH in $H_2O$ | 23 | 16 |
| 1.0 | 0.5 N LiOH in $H_2O$ | 19 | 16 |
| 0.1 | 100 percent N,N-dimethyl-benzylamine | 40 | 21 |

As is seen from Table 1, strong acid catalysts such as p-toluene sulfonic acid, used at the 0.1 mole level, gave no yield of BNA. This is also true of several other acids, including the Lewis Acid ($FeCl_3.6H_2O$) at 1 percent. It will be further noted that in the cases where no BNA was obtained, the BVE was almost wholly or at least substantially consumed in side reactions. Weak acids, i.e. those like acetic acid, gave unexpectedly improved yields. Acetic and nonanoic acids at 1 mole percent based on moles of naphthol (0.18 weight percent based on total charge) gave 72 and 69 percent yields, respectively. Tables II and III are included herein to further illustrate various methods used in an attempt to improve BNA yields.

I claim:

1. A process for making a compound of the formula

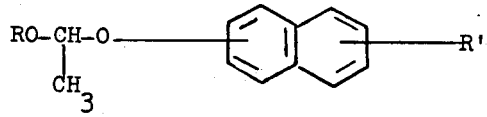

wherein R is alkyl of from 2 to 10 carbon atoms and R' is hydrogen or alkyl of from 1 to 20 carbon atoms, comprising the step of reacting a vinyl ether of the formula $ROCH=CH_2$ with a naphthol of the formula

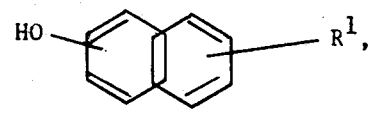

wherein R and $R^1$ are as defined above in the presence of an aliphatic monocarboxylic acid having 1 to 20 carbon atoms.

2. The process of claim 1 wherein R is butyl.
3. The process of claim 1 wherein the naphthol is 1-naphthol.
4. The process of claim 1 wherein the acid used is acetic acid.
5. The process of claim 1 wherein the acid is nonanoic acid.
6. The process of claim 1 wherein the temperature of reaction is from about 75° to about 130°C.
7. The process of claim 1 wherein the acid is present in an amount of from about 0.1 mole percent to about 5 mole percent, based on the moles of naphthol.

* * * * *